United States Patent [19]

Bowen

[11] 4,445,242

[45] May 1, 1984

[54] ABSORBENT PAD HOLDER

[76] Inventor: Charlotte M. Bowen, 2235 W. Club View Dr., Glendale, Wis. 53209

[21] Appl. No.: 365,178

[22] Filed: Apr. 5, 1982

[51] Int. Cl.³ .......................... A47G 9/04; A61G 9/00
[52] U.S. Cl. ............................................ 5/484; 5/485
[58] Field of Search ................... 5/484, 485, 487, 496, 5/498, 482

[56] References Cited

U.S. PATENT DOCUMENTS

| | | |
|---|---|---|
| 2,545,970 | 3/1951 | Rand . |
| 2,614,273 | 10/1952 | Yancofski ............................... 5/484 |
| 3,162,868 | 12/1964 | Cramer . |
| 3,974,531 | 8/1976 | Van Pelt . |
| 4,173,046 | 11/1979 | Gallagher . |
| 4,188,065 | 2/1980 | Meeker ................................ 297/485 |
| 4,316,299 | 2/1982 | Friedman ............................... 5/485 |

FOREIGN PATENT DOCUMENTS 621371 6/1961 Canada ..................................... 5/484
755077 9/1933 France .

Primary Examiner—Alexander Grosz
Attorney, Agent, or Firm—Andrus, Sceales, Starke & Sawall

[57] ABSTRACT

A holder for an absorbent pad used to protect seat cushions or the like from body fluids. The holder includes a cover having a length sufficient to wrap around the cushion, and a panel sewn to the inner surface of the cover to provide a pocket for receiving an absorbent pad. The panel and pocket are positioned so that the pad substantially overlies the sitting portion of the cushion and extends downwardly along the front portion of the cushion. The ends of the cover are removably fastened to one another to prevent movement or displacement of the pad.

8 Claims, 3 Drawing Figures

ABSORBENT PAD HOLDER

BACKGROUND OF THE INVENTION

The present invention relates to protective covers for seat cushions or the like, and more particularly to a holder for an absorbent pad used to protect seat cushions or the like from body fluids.

In hospitals, nursing homes and the like many patients are incontinent and are unable to restrain natural discharges, such as urine, from the body. It is thus desirable to provide protective covers for seat cushions and the like so that the cushions remain moisture and odor free.

Protective covers for various types of devices have been utilized in the past. U.S. Pat. Nos. 3,974,531, 3,162,868, and 2,545,970 show protective covers for pillows, while U.S. Pat. Nos. 4,188,065, 4,173,046 and 2,614,273 show structures for protecting infant seats, beds and cribs, respectively. In particular U.S. Pat. No. 2,614,273 shows an assembly wherein an absorbent pad is slidably received within a pocket formed by a waterproof bottom piece and a perforated top piece. Such an assembly, however, would be impractical for use with seat cushions for chairs since there is nothing to prevent the movement or displacement of the pad and its cover as patients repeatedly sit down and arise from the chair.

SUMMARY OF THE INVENTION

A holder for an absorbent pad used to protect seat cushions or the like from body fluids. The holder includes a cover of sufficient length to wrap around the cushion, a panel attached to the inner surface of the cover to provide a pocket for receiving an absorbent pad, and fastening means for removably fastening the ends of the cover to one another to prevent displacement of the pad. The panel and pocket are positioned so that the pad will substantially overlie the sitting portion of the cushion.

The opening of the pocket formed by the panel is coextensive with the width of the cover to permit easy insertion and removal of the absorbent pad, and the cover itself preferably has a width substantially equal to the width of the seat cushion to insure protection of the entire sitting portion of the cushion. The panel and pocket are of sufficient length that the pad extends downwardly along the front portion of the cushion to also protect that area of the cushion.

The absorbent pad may be disposable, and the cover and panel may be constructed of an easily washable material so that the pad holder may be maintained odor free.

BRIEF DESCRIPTION OF THE DRAWINGS

The drawings illustrate the best mode presently contemplated of carrying out the invention.

In the drawings.

DESCRIPTION OF THE PREFERRED EMBODIMENT

Figure 1:
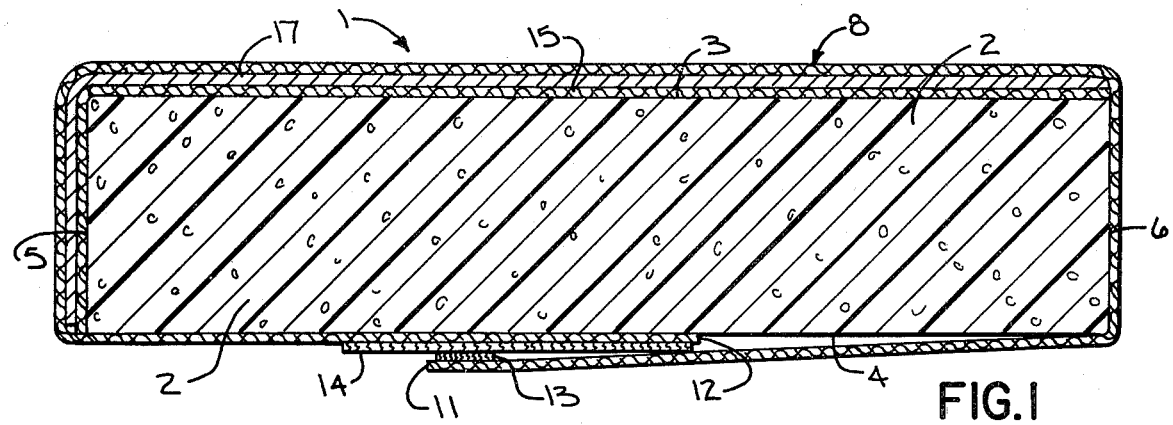
FIG. 1 is a side view in elevation illustrating an absorbent pad holder assembly in accordance with the principles of the present invention.
Figure 2:
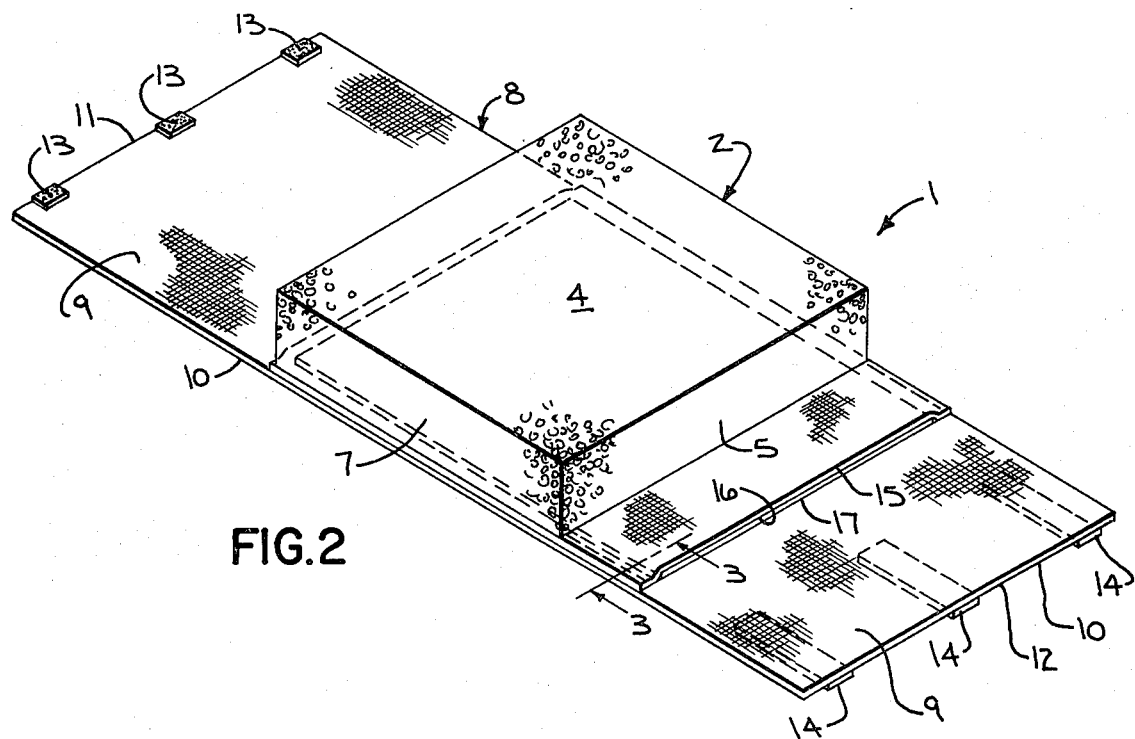
FIG. 2 is a view in perspective of the absorbent pad holder assembly of FIG. 1 with the cover unwrapped from the cushion.

Referring now to the drawings, FIGS. 1 and 2 illustrate an absorbent pad assembly 1 adapted to be wrapped around a cushion 2 for a chair or the like. The pad assembly 1 is designed for use in a nursing home, hospital, private home or the like for protecting the cushion 2 from absorbing body fluids, such as urine, discharged by incontinent patients who are unable to restrain their natural discharges.

The cushion 2 may be of any conventional design for use on a chair, or may be in combination with other cushions for use on a sofa. The cushion 2 may be constructed of polyurethane foam or any other similar foam product commonly used as cushion material. The cushion 2 includes a top surface 3, a bottom surface 4, front and rear portions 5 and 6 and a pair of side portions 7. The top surface 3 is the sitting portion of cushion 2, as shown best in FIG. 1. It should be noted that the top surface 3 faces upwardly in FIG. 1, but faces downwardly in FIG. 2.

Referring now to FIG. 2, the pad assembly 1 includes a cover 8 which is rectangular in shape having its length greater than its width. The cover 8 defines a pair of oppositely disposed inner and outer surfaces 9 and 10, respectively, with the inner surface 9 facing the cushion 2 and the outer surface 10 facing away from cushion 2. The cover 8 is of sufficient length that it may be wrapped around the cushion 2 so that its ends 11 and 12 extend around to the bottom of underside surface 4 of cushion 2 to substantially surround cushion 2. The width of cover 8, as shown in FIG. 2, is substantially identical to the width of cushion 2. The cover 8 may be constructed of any easily washable material such as cotton, so that it may be washed in any conventional manner and be maintained odor free.

As shown in FIG. 1 the ends 11 and 12 of cover 8 overlap one another along the underside of cushion 2, and fastening means disposed adjacent the ends 11 and 12 are included for removably fastening the ends 11 and 12 to one another, as shown in FIG. 1. One end 11 of cover 8 contains three spaced hook and loop type fastener, such as the one sold under the trademark of Velcro 13 attached to the inner surface 9 while the opposite end 12 contains three spaced back and loop type fastener fasteners 14 attached to the outer surface 10 of cover 8. As shown, each fastener 14 has a length which is greater than its width with its length extending in the same direction as the length of cover 8. Fasteners 14 thus enable the cover 8 to be snugly wrapped around different size cushions 2. In order to fasten cover 8 around cushion 2, the ends 11 and 12 are simply overlapped as shown in FIG. 1 and the fasteners 13 and 14 pressed against each other to fasten the inner surface 9 of end 11 to the outer surface 10 of end 12.

The pad assembly 1 also includes a panel 15 attached to the inner surface 9 of cover 8. The panel 15 is sewn to the cover 8 on three sides along its periphery to provide a pocket 16 having an opening facing the end 12 of cover 8. The opening for pocket 16 is coextensive with the width of cover 8, and the length or depth of pocket 16 is such that pocket 16 substantially overlies the sitting portion 3 and front portion 5 of cushion 2.

Figure 3:
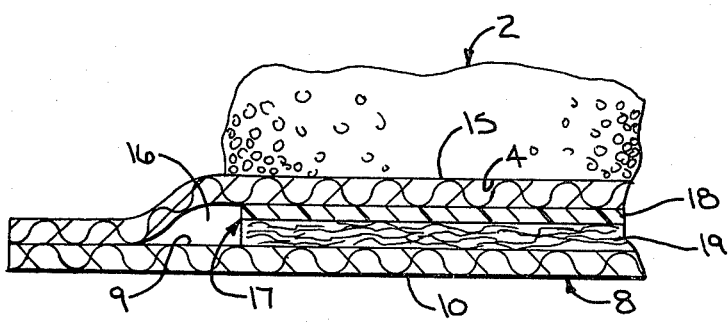
FIG. 3 is a view in cross section taken along the plane of the line 3—3 in FIG. 2.

A disposable absorbent pad 17 is positioned in pocket 16 between the panel 15 and the inner surface 9 of cover 8. The pad 17 has a width and length substantially identical to the pocket 16 so that it may be easily slidably inserted and removed from pocket 16. Thus, pad 17 has a length sufficient to overly the sitting portion 3 and front portion 5 of cushion 2, and a width substantially equal to the width of cushion 2. Referring now to FIG. 3, the pad 17 includes an impervious layer 18 disposed adjacent to the panel 15, and an absorbent layer 19 disposed adjacent to the inner surface 9 of cover 8. Thus, if urine was to be discharged by an incontinent patient while sitting on cushion 2 the urine would flow through the cover 8 (in an upward direction in FIG. 3) into the absorbent layer 19 of pad 17 whereupon the imprevious layer 18 would prevent the urine from being absorbed into cushion 2.

In operation, the pad holder assembly 1 is wrapped around the cushion 2 so that the pad 17 is positioned on the sitting portion of cushion 2 with the absorbent layer 19 upwardly and the impervious layer 18 downwardly, as shown in FIG. 1, so as to prevent human fluids from entering and being absorbed by cushion 2. A portion of pad 17 is positioned to extend downwardly along the front portion 5 of cushion 2 as an added measure of protection for the front 5 of cushion 2. Once the pad 17 is properly positioned the ends 11 and 12 of cover 8 are fastened to one another by means of the hook and loop type fastener fasteners 13 and 14.

When it is desired to remove and replace pad 17 the ends 11 and 12 of cover 8 are merely pulled apart and the end 12 is extended outwardly to the left, as seen in FIG. 1, until the end 12 is in about the same plane as the sitting portion 3 of cushion 2. The pad 17 is then grasped along its edge and removed from pocket 16 and disposed of. The cover 8 and panel 15 may then be washed in any conventional manner. A fresh pad 17 may then be inserted into the pocket 16 of a fresh cover 8 and panel 15 and wrapped around the cushion 2 so that pad 17 is once again properly positioned on the sitting portion 3 of FIG. 2, as previously described. The ends 11 and 12 may then be fastened to one another utilizing the hook and loop type fastener fasteners 13 and 14.

Various modes of carrying out the invention are contemplated as being within the scope of the following claims particularly pointing out and distinctly claiming the subject matter which is regarded as the invention.

I claim:

1. A holder for an absorbent pad used to protect seat cushions or the like from body fluids, comprising:
    a cover having first and second ends and defining oppositely disposed inner and outer surfaces, said cover having a sufficient length such that said first and second ends extend around to the underside of a cushion;
    fastening means disposed adjacent said first and second ends for removably fastening said ends to one another; and
    a panel attached to the inner surface of said cover along its periphery except for one side thereof to provide a pocket having an opening receiving an absorbent pad, said panel and pocket positioned so that the pad will substantially overlie the sitting portion of a cushion, said pad including an impervious layer disposed adjacent to said panel and an absorbent layer disposed adjacent to said inner surface.

2. The pad holder of claim 1, wherein the first and second ends of said cover overlap one another, and said fastening means fastens the inner surface of one of said ends with the outer surface of the other of said ends.

3. The pad holder of claim 1, wherein the opening of said pocket is coextensive with the width of said cover.

4. The pad holder of claim 1, wherein said panel defines a pocket of sufficient length so that said pad may overlie the sitting portion and front portion of a cushion.

5. An absorbent pad holder assembly for protecting seat cushions or the like from body fluids, comprising:
    a cover having first and second ends and defining oppositely disposed inner and outer surfaces, said cover having a sufficient length such that said first and second ends extend around to the underside of a cushion to substantially surround a cushion;
    fastening means disposed adjacent said first and second ends for removably fastening said ends to one another;
    a panel attached to the inner surface of said cover along its periphery except for one side thereof to provide a pocket having an opening coextensive with the width of said cover and facing one of said ends, said panel and pocket adapted to be positioned to substantially overlie the sitting portion of a cushion; and
    an absorbent pad disposed in said pocket between said panel and the inner surfce of said cover, said pad including an impervious layer disposed adjacent to said panel and an absorbent layer disposed adjacent to said inner surface.

6. The pad holder assembly of claim 5, wherein the first and second ends of said cover overlap one another, and said fastening means fastens the inner surface of one of said ends with the outer surface of the other of said ends.

7. The pad holder assembly of claim 5, wherein the opening of said pocket is coextensive with the width of said cover.

8. The pad holder assembly of claim 5, wherein said pad has a length sufficient to overlie the sitting portion and front portion of the cushion and a width substantially equal to the width of the cushion.

* * * * *

UNITED STATES PATENT AND TRADEMARK OFFICE
CERTIFICATE OF CORRECTION

PATENT NO. : 4,445,242
DATED : May 1, 1984
INVENTOR(S) : CHARLOTTE M. BOWEN

It is certified that error appears in the above-identified patent and that said Letters Patent are hereby corrected as shown below:

| | |
|---|---|
| Col. 2, Line 31 | after "bottom" delete "of" and substitute therefor ---or--- |
| Col. 2, Lines 44-45 | delete "Vel-cro" and substitute therefor ---VEL-CRO--- |
| Col. 2, Lines 46-47 | after "type" delete "fas-tener" |
| Col. 3, Line 2 | delete "overly" and substitute therefor ---overlie--- |
| Col. 3, Line 27 | after "type" delete "fastener" |
| Col. 3, Line 43 | after "type" delete "fastener" |
| Claim 5 Col. 4, Line 41 | delete "surfce" and substitute therefor ---surface--- |

Signed and Sealed this

Thirtieth Day of October 1984

[SEAL]

Attest:

GERALD J. MOSSINGHOFF

Attesting Officer     Commissioner of Patents and Trademarks